(12) United States Patent
Nilsson et al.

(10) Patent No.: US 6,422,236 B1
(45) Date of Patent: Jul. 23, 2002

(54) CONTINUOUS DRY POWDER INHALER

(75) Inventors: Thomas Nilsson, Mariefred; Mattias Myrman, Stockholm, both of (SE)

(73) Assignee: Microdrug AG, Hergiswil NW (CH)

( * ) Notice: Subject to any disclaimer, the term of this patent is extended or adjusted under 35 U.S.C. 154(b) by 0 days.

(21) Appl. No.: 09/690,017

(22) Filed: Oct. 17, 2000

(30) Foreign Application Priority Data

Sep. 25, 2000 (SE) ............................................. 0003408

(51) Int. Cl.$^7$ ............................................. A61M 15/00
(52) U.S. Cl. ................................................. 128/203.15
(58) Field of Search ...................... 128/200.11, 200.12, 128/200.14, 200.16–200.18, 200.21–220.24, 203.12, 203.15, 203.21; 604/58; 116/311–315, 318, 319

(56) References Cited

U.S. PATENT DOCUMENTS

| | | | |
|---|---|---|---|
| 5,035,237 A | * 7/1991 | Newell et al. | 128/203.15 |
| 5,042,472 A | * 8/1991 | Bunin | 128/203.15 |
| 5,207,217 A | * 5/1993 | Cocozza et al. | 128/203.21 |
| 5,320,095 A | * 6/1994 | Nijkerk et al. | 128/203.15 |
| 5,333,106 A | * 7/1994 | Lanpher et al. | 128/200.12 |
| 5,408,994 A | * 4/1995 | Wass et al. | 128/203.15 |
| 5,415,162 A | * 5/1995 | Casper et al. | 128/203.12 |
| 5,452,711 A | * 9/1995 | Gault | 128/200.14 |
| 5,642,727 A | * 7/1997 | Datta et al. | 128/203.15 |
| 5,758,638 A | * 6/1998 | Kreamer | 128/200.23 |
| 5,921,232 A | * 7/1999 | Yokoi et al. | 128/200.14 |
| 5,970,974 A | * 10/1999 | Van Der Linden et al. | 128/200.16 |
| 6,182,655 B1 | * 2/2001 | Keller et al. | 128/203.15 |
| 6,220,243 B1 | * 4/2001 | Schaeffer et al. | 128/203.15 |
| 6,273,084 B1 | * 8/2001 | Frid | 128/200.23 |
| 6,273,085 B1 | * 8/2001 | Eisele et al. | 128/203.15 |
| 6,321,747 B1 | * 11/2001 | Dmitrovic et al. | 128/203.15 |
| 6,360,744 B1 | * 3/2002 | Myrman et al. | 128/203.15 |

* cited by examiner

*Primary Examiner*—John G. Weiss
*Assistant Examiner*—Teena Mitchell
(74) *Attorney, Agent, or Firm*—Young & Thompson

(57) ABSTRACT

An continuous dry powder inhaler arrangement is disclosed, the arrangement being provided with electrostatically dosed medical powder onto an exchangeable dosing member like a cassette or the like for respiratory administration of medicaments into the deep or upper lung airways. The inhaler presents a compact integrated device (8) with a case having a sliding lid (17), which can be set in an open position exposing a mouthpiece (19) or in a closed position. The arrangement further provides dose (18b/18c) counters and a cassette counter (34). In the state with open lid (17) the device is ready to deliver a prepared pre-metered dose of medical powder upon an inhalation via the exposed mouthpiece (19). Medical drugs are in advance dosed as medical powder and carried by an exchangeable dosing means and constitute dry powder substances or dry powder medical formulations prepared for continuous dosing during a preset period of operation. The exchangeable dosing member carries a number of sequentially accessible doses, which are sealed to preserve a controlled storing of powder during the total lifetime of the dosing member. The sealing is cut open during an inhalation process after that the device has been set into the open state by moving the sliding lid (17) to the open position. Upon an inhalation the cassette carrying a selected dose is released into a longitudinal motion by a forcing spring, whereby the protective foil is cut open to let a nozzle of a suction tube access the powder. By means of a braking arrangement the motion of the cassette is adjusted to such a speed that the time for a continuous delivery of the powder will be prolonged to an order of 1 to 2 seconds. The exchangeable dosing means presents a number of electrostatically deposited dry medical powder.

17 Claims, 11 Drawing Sheets

CONTINUOUS DRY POWDER INHALER

TECHNICAL FIELD

The present invention relates to administration of medical powders into the respiratory tract by releasing powder to be inhaled and more particularly to a dry powder inhaler dispensing a pre-metered dose of medical powder during a prolonged inhalation process.

BACKGROUND

The administration of drugs is carried out in a number of different ways in the medical service today. Within health care more and more is focussed on the possibility to dose and distribute powder directly to the lungs of a user by means of an inhaler to obtain effective, quick, and user friendly administration of such substances.

A dry powder inhaler of today, (DPI), represents a device intended for administration of powder into the deep or upper lung airways by oral inhalation. With deep lung should be understood the peripheral lung and alveoli, where direct transport of active substance to the blood can take place. Particle sizes, to reach into the deep lung, should be in a range 0.5–3 $\mu$m and for a local lung delivery in the range 3–5 $\mu$m. A larger grain size will easily stick in the mouth and throat, and a smaller grain size may accompany the expiration air out again.

Administration of medical powders into the respiratory tract is a very attractive way for administration of many substances both for local treatments and for systemic treatments. To administer electrostatically dosed drugs by a dry powder inhaler (DPI) through the lung some very important technical basic factors must be met by the system.

A correct dose with a high uniformity of dose is desired from the inhaler. For electrostatically dosed medical substances the relative standard deviation between doses (RSD) should preferably be not more than 5%.

However, powder having a small grain size will demonstrate a strong tendency to agglomerate, i.e. to clod into larger grains. In the inhalers being used at the moment a large portion of the powder is agglomerated when it is dosed and much powder therefore will stick to the upper respiratory tracts. Technologies for de-agglomeration include advanced mechanical and aerodynamic systems and combinations between electrical and mechanical filling systems that can be seen in for instance U.S. Pat. No. 5,775,320, U.S. Pat. No. 5,785,049 and U.S. Pat. No. 5,740,794.

It is also common to utilize carriers having a larger grain size onto which the fine power is distributed. Upon inspiration the large size grains will stick in the oral cavity while the small grains will be let free and proceed to the lung.

One of the problems upon inhalation of a medical powder is that a relatively large portion of the dose will also stick in the inhaler device. To be able to include all powder and disassemble agglomerates a high air velocity is needed. From a dose given by the inhaler the respiratory dose (grain size less than 5 μm) may often be only 20%.

For achieving a high respiratory dose often a socalled spacer is used to have the small grains evenly distributed in a container from which the inhalation can take place. In principle a dosing device or an inhaler is connected to a container having a relatively large volume and into this container a powder or an aerosol is injected which partly is distributed in the air space and partly sticks to the walls. Upon inhalation from the spacer the fine powder floating free in the air will effectively reach the alveoli. This method in principle has two drawbacks, firstly difficulties to control the amount of medicine emitted to the lung as uncontrolled amount of powder sticks to the walls of the spacer and secondly difficulties in handling the relatively space demanding apparatus to be desired when it comes to dosage conformity and lung deposition effectiveness of the medical substance.

To meet some of these demands an electrostatic dosing of the powder onto a technical means for example a cassette can by done. An electrostatic dosing onto a device member or cassette was described in our Swedish Patent No. 9802648-7 (SE512 433) and the quality can be improved by utilizing the possibility to classify coarse particles larger than 5 μm to leave those out and dose only fine particles (less than 5 μm) onto the device member or cassette as described in our Swedish Patent No. 9802649-5 (SE512 386).

However, still there is a demand for a device sampling administration of medical powder by means of an inhaler providing a compact arrangement without the need for instance for a space demanding spacer.

SUMMARY

A continuous dry powder inhaler arrangement is disclosed, the arrangement being provided with electrostatically dosed medical powder onto an exchangeable dosing means like a cassette or the like for respiratory administration of medicaments into the deep or upper lung airways. The inhaler presents a compact integrated device with a case having a sliding lid, which can be placed in a closed position covering a mouthpiece or in an open position exposing this exchangeable mouthpiece. In the open lid position the device is ready to deliver a prepared pre-metered dose of medical powder upon-an inhalation via the exposed mouthpiece. Medical drugs are in advance dosed as medical powder and carried by an exchangeable dosing means and constitute dry powder substances or dry powder medical formulations prepared for continuous dosing. The exchangeable dosing member carries a number of sequentially accessible sealed doses. The sealing of the individual doses preserves a controlled storing, of powder during the total lifetime of a dosing cassette. This sealing is cut open during the inhalation process after that the device has been set into the open state by moving the sliding lid to the open position. The mouthpiece and/or the exchangeable dosing means of the device is preferably made out of dissipative and conductive materials to prevent electrostatic charge build-up during inhalation. Upon an inhalation the cassette carrying a selected dose is released into a longitudinal motion by a forcing spring, whereby the protective foil is cut open to let a nozzle of a suction tube access the powder. By a braking arrangement, the motion of the cassette is adjusted to such a speed that the time for the continuous delivery of the powder will be controlled and prolonged to an order of 0.5 to 5 seconds. The exchangeable dosing means normally presents a number of electrostatically deposited dry medical powder doses in the form of strips or a series of spots onto the dosing means. The DPI is adjusted for a systemic or a local lung setting with respect to activation pressure and closing pressure resulting in a 20 to 60 liter/minute inhalation air flow for systemic delivery setting and 40 to 80 liters/minute for a local lung setting. Furthermore the de-agglomeration power is adjusted between 0.1 and 6 watts to be used in the DPI by optimizing the pressure drop and inhalation flow rate by changes to the mouthpiece and/or the device member and their relation to each other. The DPI activation pressure is further adjusted to a value between 0.5 and 4 kPa and closing pressure between 0.5 and 4 kPa to eliminate the low power at the start and end of the inhalation. The inhaler arrangement further provides a number of special functions for a safe handling of the device, e.g. control of regular changes of mouthpiece and controls for a utilization of a pre-defined number of cassettes after which it must be discarded.

BRIEF DESCRIPTION OF THE DRAWINGS

The invention, together with further objects and advantages thereof, may best be understood by making reference to the following description taken together with the accompanying drawings, in which.

DESCRIPTION

General Definition of the Inhaler Arrangement

The present invention discloses a dry powder inhalation device (DPI) providing a continuous prolonged delivery of a pre-metered dose during an inhalation of its medical powder or powders. The pre-metered dose is preferably a dose of electro-powder presenting well defined characteristics regarding for instance, particle sizes, electrostatic characteristics, water content and so on. The arrangement comprises in an illustrative embodiment a body, an exchangeable mouthpiece with a suction tube and an exchangeable moving cassette carrying pre-metered sealed doses of dry powder applied in the form of strips or series of spots of powder.

Figure 5:
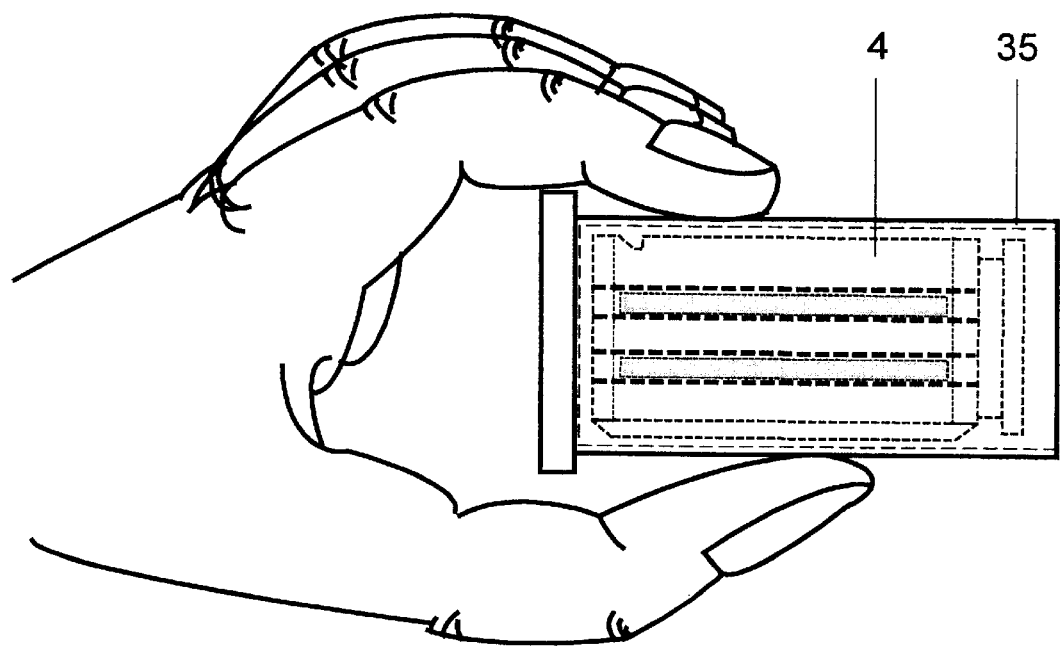
FIG. 5 illustrates how the cassette and a box protecting it can be held.

Prefabricated cassettes are individually packed in airtight packages. A cassette box protects the cassette such that when the package is opened and the cassette is removed the user does not come in contact with the sealed doses. The mechanically coded cassette and cassette box are inserted into an opening into the body of the inhaler arrangement according to the present invention. (Also see FIGS. 5 and 6) The cassettes intended for the purpose are correspondingly coded such that only the correct type of cassette fits the opening. Such a coding eliminates the risk that a cassette carrying different powders than the intended can be inserted into an actual inhaler.

Figure 7:
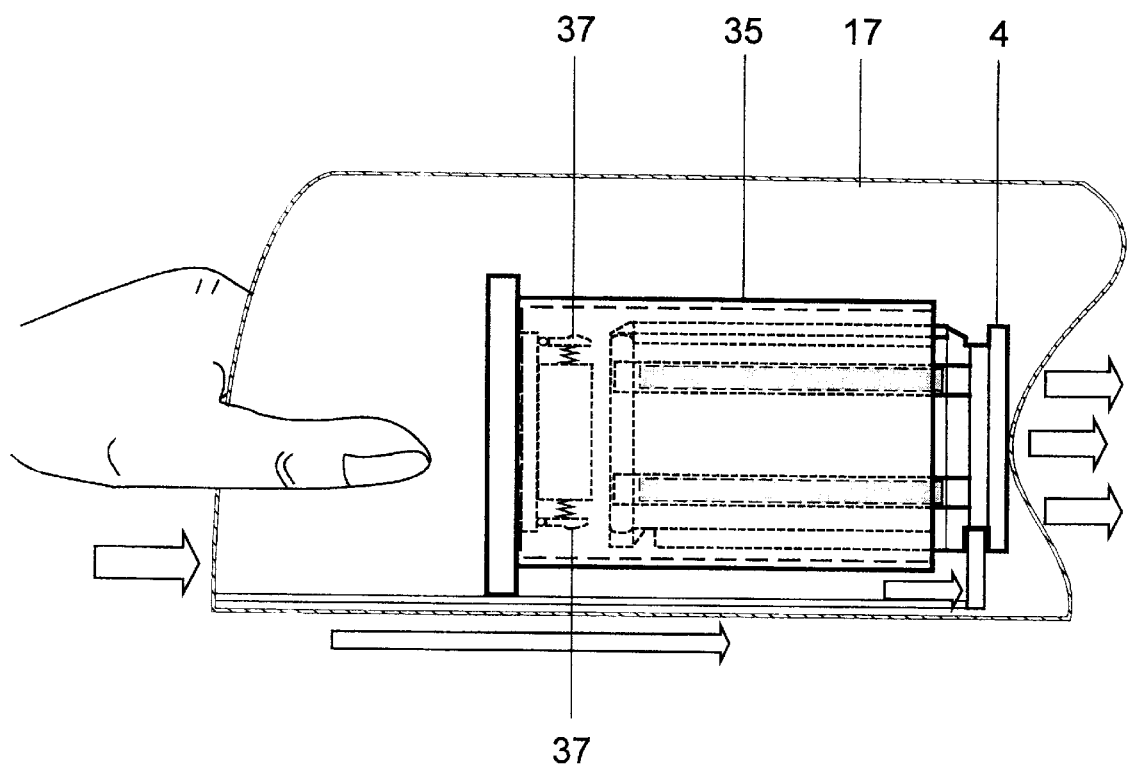
FIG. 7 shows in an illustrative embodiment the mechanism of extracting the cassette from the cassette box and the loading of the cassette into the body of the DPI as the user pushes the cover of the DPI in the closed position.
Figure 8:
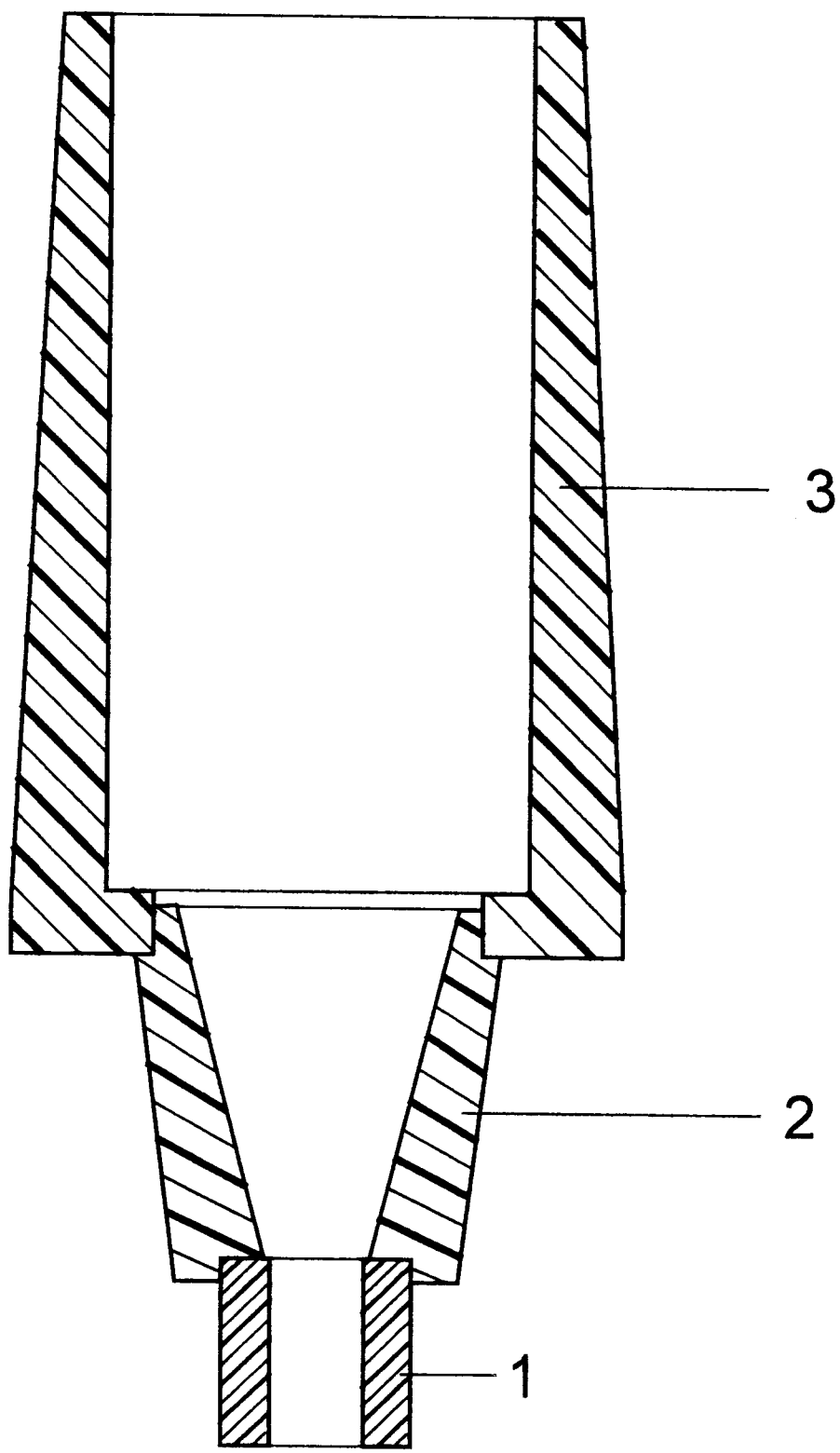
FIG. 8 shows in an illustrative embodiment the suction tube.
Figure 9:
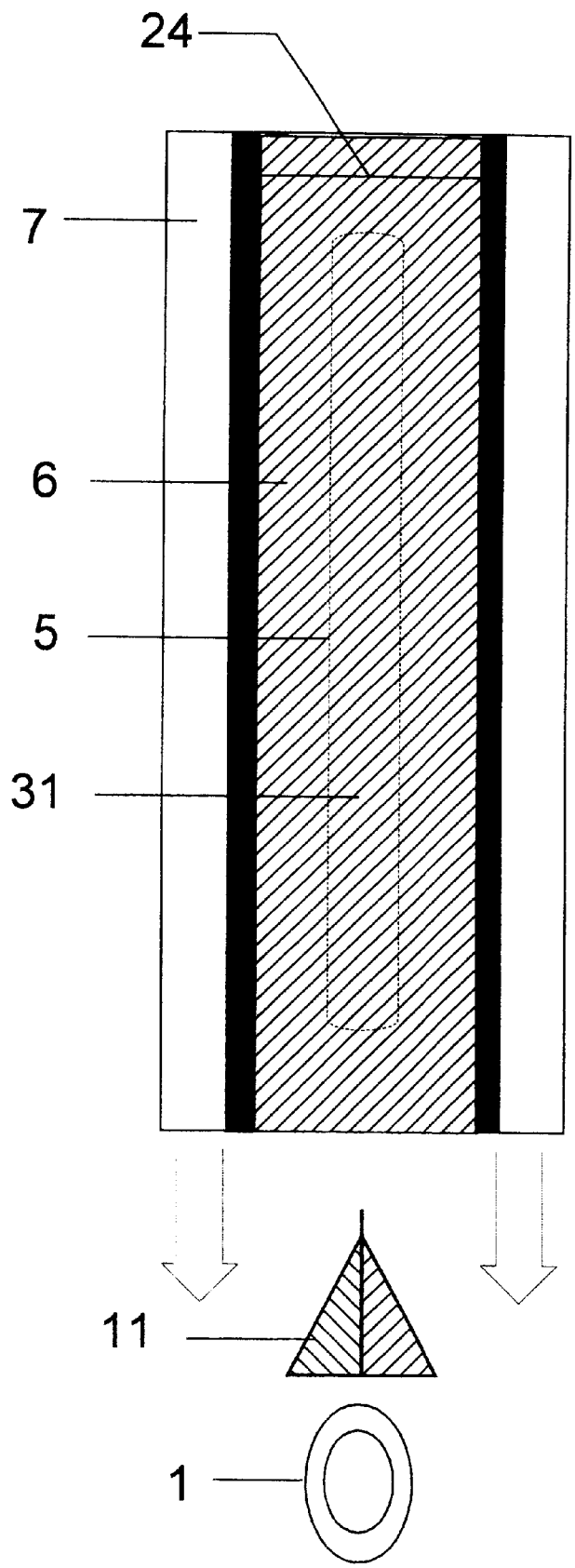
FIG. 9 shows in an illustrative embodiment one of the pre-metered doses onto the cassette and covered by a protective foil, which will be cut open by a cutter tool when the cassette is propelled in direction of the arrows.

Before the first dose on the cassette can be administered the inhaler must first be opened and closed by pulling the covering lid open and then pushing it shut again. In this way the cassette is extracted from the protective box, schematically illustrated in FIG. 7, and brought in the loaded position at the same time as a cassette drive spring is tensioned and secured in this mode by a plunger element.

Removing the cover by pulling it to the side reveals the mouthpiece to which the suction tube is affixed. Thus the cover protects the inhaler and especially the mouthpiece from dirt etc. when the inhaler is not in use. In the process of pulling the cover open the plunger element securing the cassette is pulled out, but the cassette is still kept in the loaded position by another catch mechanism.

The body houses a system for triggering and controlling the administration by means of the inhaler arrangement of pre-metered doses from the cassette, normally a medical drug but other substances are also possible. The system for triggering the delivery of the dose to the user utilizes the inhalation effort to release the catch mechanism that keeps the cassette in its initial spring loaded position as well as opens an inlet for outside air to enter into the interior of the inhaler.

Figure 10:
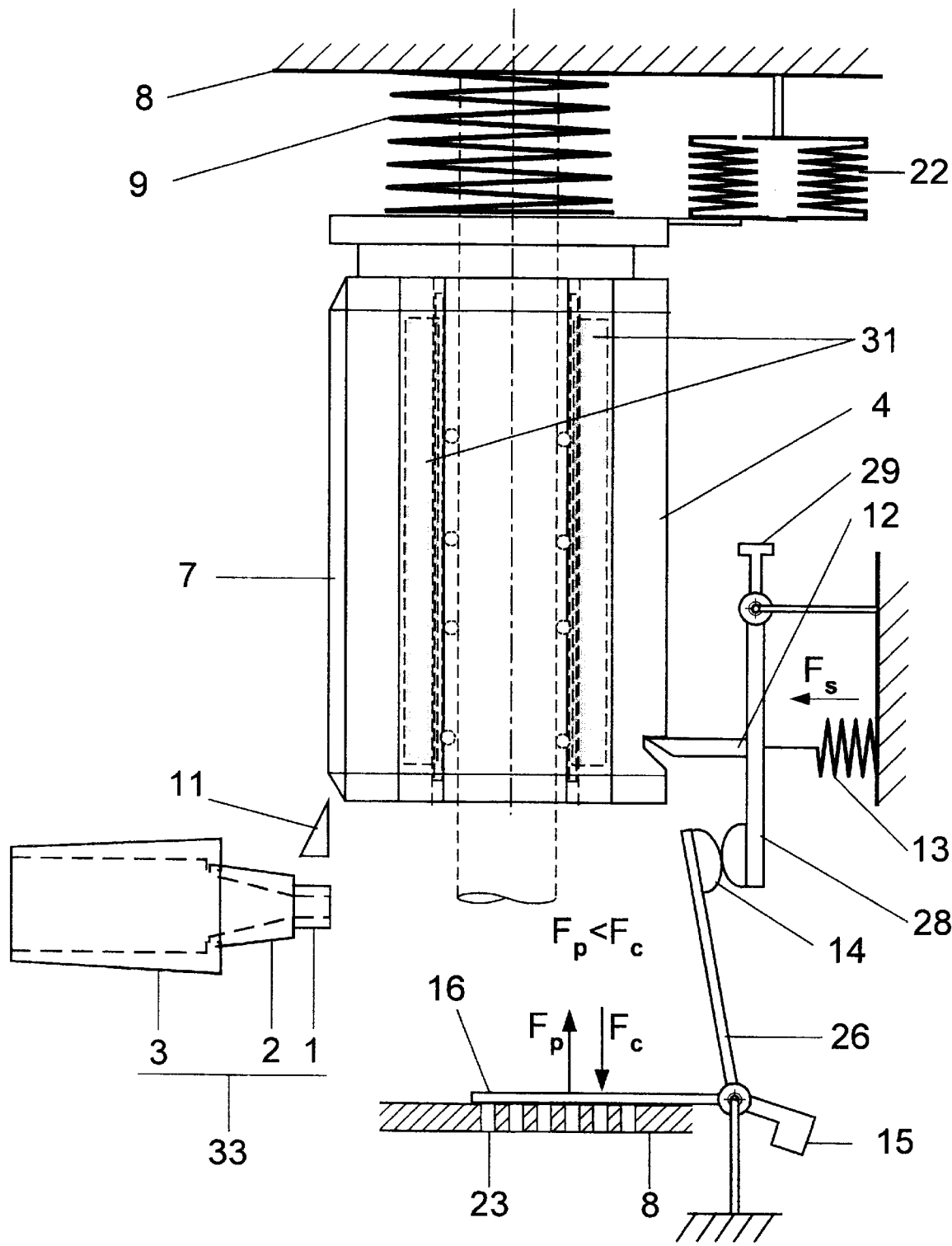
FIG. 10 illustrates in an illustrative embodiment the most important internal parts and mechanisms controlling the process of administering a pre-metered dose of powder to a user.
Figure 11:
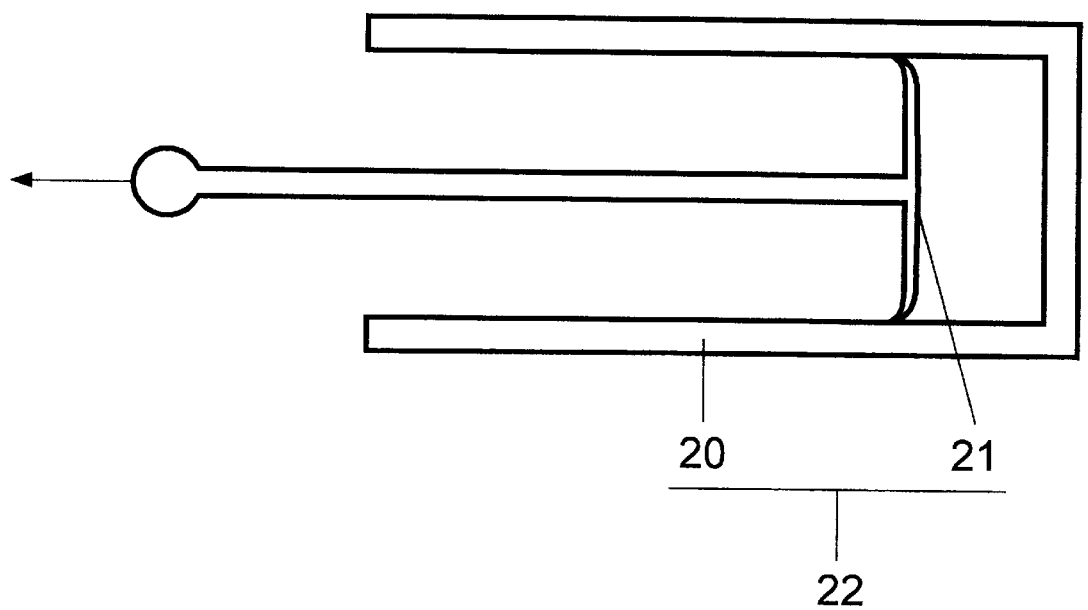
FIG. 11 illustrates one embodiment of the airbrake arrangement for controlling the motion of the cassette during the inhalation process.
Figure 12:
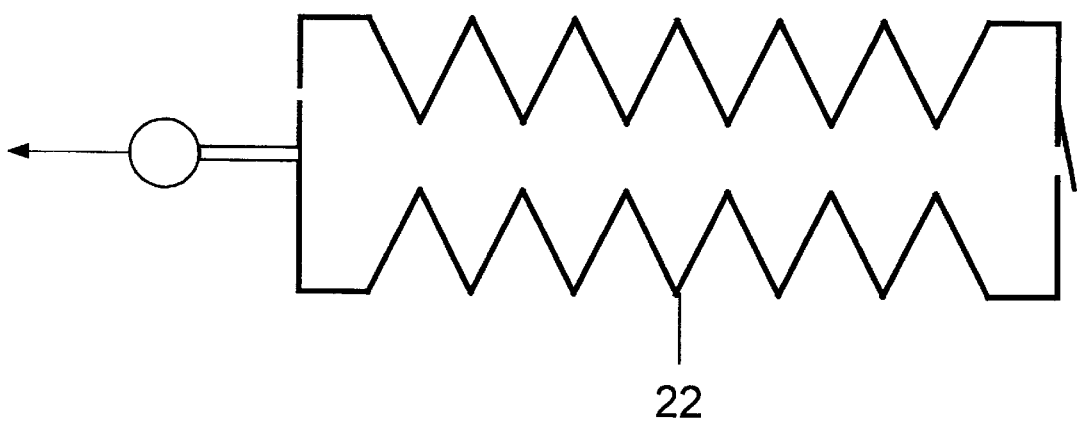
FIG. 12 illustrates another embodiment of the airbrake arrangement.
Figure 13:
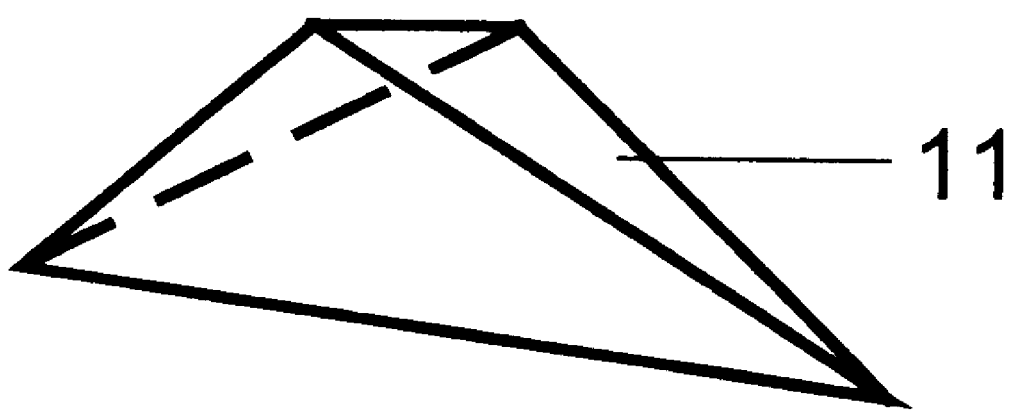
FIG. 13 illustrates an embodiment of the foil-cutter device.

A flap closes the air inlet tightly when the user is not inhaling. The closing force emanates from a spring acting through a system of levers on the catch mechanism and on the flap. When the user starts to inhale a differential pressure between the surrounding atmosphere and the airways of the user is induced. The induced differential pressure gives rise to an opening force $F_p$, which counteracts the closing force $F_c$ on the flap. When the differential pressure reaches and supersedes a minimum value the resulting opening force $F_p = F_{minimum}$ overcomes the net closing force $F_c$ of the spring, releasing the catch and opening the flap so that air starts to flow into the inhaler. Referring to FIG. 10 it is realized that the minimum required opening force corresponding to a minimum value of differential pressure can easily be adjusted by using a different spring 13 with a different rate, or changing the positions of the pivot points for the levers 28 and 26, or by using a different lever geometry, or a combination of these methods. In this way the required minimum force $F_p = F_{minimum}$ to open the flap can easily be chosen to suit the particular DPI and serve the objectives of the DPI to the best advantage. The DPI activation pressure is further adjusted to a value between 0.5 and 4 kPa and closing pressure between 0.5 and 4 kPa to eliminate the low power at the start and end of the inhalation.

A system of levers, which connect the spring with the catch and the flap are preferably designed using suitable low-friction materials and arranged such that the surfaces of the parts, which are in contact in order to transmit power from one to the other or vice versa, are made with rounded shapes and arranged such that the inevitable relative movement is not a rubbing action but a rolling action, such that the point of contact moves like two cogs meshed in a gear wheel to minimize friction in the system. In this way the friction losses and power loss in the mechanical system are minimized, which is important to achieve optimum overall performance for the DPI.

When the catch releases the cassette it is irreversibly propelled forward by the tensed drive spring. An airbrake, which acts on the cassette controls the speed of motion of the cassette such that the time it takes for the cassette to pass by the fixed suction tube of the mouthpiece can be controlled as desired. The powder of the dose to be administered is in this way carried by the cassette past the fixed nozzle of the suction tube where a passing stream of air rushing into the nozzle of the suction tube sucks up the powder.

It is particularly important that particle size distribution and uniformity of dose is user independent. Each dose on the cassette carrier has an individual airtight seal in the form of an aluminum strip or the like, which must be cut open before the dose can be accessed. A sharp cutter in the shape of a wedge with a sharp edge is in a fixed position just before the nozzle such that when the cassette begins to move, the seal of the dose is brought in contact with the cutter before the dose reaches the nozzle. The cutter not only cuts the foil open but it also folds back the foil to make the powder completely accessible for the stream of incoming air resulting from the inhalation.

In different embodiments of the present invention, the drive spring and the airbrake can be given different properties to achieve the desired speed characteristics for the cassette in each embodiment depending on what is the primary purpose of the inhaler in each case. The active dosing time of the DPI during an inhalation can be set for an activation time between 0.5 and 5 seconds. The cassette and airbrake are arranged such that there is a time delay after the catch lets go of the cassette until the first part of the dose reaches the point where the powder of the pre-metered dose will be sucked up by the inhaled air.

The powder is sucked up by the stream of air going into the nozzle at high speed. Further up the suction tube the air speed becomes reduced and the powder is evenly dispersed in the air stream. The suction tube is specially designed using porous walls such that a minimum of powder is retained in the mouthpiece and practically all powder is delivered into the user in continuous manner during a predefined time period. The cassette reaches its end position in about 0.5 to 2 seconds after it was released. The user pushes the covering lid to the closed position and leaves the inhaler locked in this way until it is time for a new dose.

A dose indicator in the form of a counter indicates when the last dose of a cassette has been administered and at this point the revolver mechanism stops any further inhalation cycles with the old used up cassette, but releases the cassette from the DPI, so the user can remove the old cassette and replace it with a new one.

Every time a predetermined number of cassettes have been utilized in the inhaler a cassette indicator in the form of a counter indicates that it is time to exchange the mouthpiece. The interval between changes of mouthpiece is short enough to keep a high level of hygiene and to eliminate the risk that retained powder in the suction tube builds up to a point where it risks becoming unstuck during an inhalation, giving the user too high a dose. The mouthpiece can easily be removed and replaced with a new one by the user.

When the cassette counter reaches the zero point the DPI is by definition worn out. When all doses of the last cassette have been administered the cassette counter mechanism locks the cassette in the DPI so it cannot be removed from the DPI. The user is left with no option but td. discard the whole inhaler including the last cassette and get a new inhaler if further medication is necessary.

Description of a Preferred Embodiment of the Continuous Inhaler Device

The exterior of the inhaler device is schematically illustrated in FIGS. 2, 3 and 4. Pulling a cover 17 opens the DPI and gives the user access to the mouthpiece 19, which is used for inhaling dosed medical powder through the DPI. Pushing the covering lid back into the initial position closes and locks the arrangement. During storage and transportation the DPI should be in the closed state such that the cover 17 gives adequate protection of the mouthpiece 19 against ingress of dirt etc. The inhaler body houses a system for triggering and controlling the administration of the doses of dry powder from the dose carrier, referred to as a cassette 4 (FIGS. 5, 6 and 7), to be handled by the user utilizing the device for inhaling dry powder normally being a medical drug, even if other substances are also possible.

The mouthpiece 19 comprises a suction tube 33 (FIG. 10) and a mechanism for attaching the exchangeable mouthpiece to the body 8 of the DPI. Once the user has opened the DPI he or she has easy access to the comfortably formed mouthpiece with the top end of the suction tube arranged to make the inhalation as easy as possible for a user. The DPI is adjusted for a systemic or a local lung setting with respect to activation pressure and closing pressure resulting in a 20 to 60 liter/minute inhalation air flow for systemic delivery setting and 40 to 80 liters/minute for a local lung setting. Furthermore the de-agglomeration power is adjusted between 0.1 and 6 watts to be used in the DPI by optimizing the pressure drop and inhalation flow rate by changes to the mouthpiece and/or the device member and their relation to each other. The material of the mouthpiece in contact with the user's mouth is preferably electrically dissipative or conductive so as to equalize any difference in the electric potential between the user and the DPI such that the delivery of the dose is not negatively affected by potential differences. When a predetermined number of cassettes have been administered through the inhaler a built in cassette counter 18*a* (FIG. 3) indicates that it is time to exchange the mouthpiece and prompts the user to do this. The interval between changes of mouthpiece is short enough to keep a high level of hygiene and to eliminate the risk that retained powder builds up in the suction tube 33, which comprises a nozzle 1, a diffuser 2 and a porous tube 3. Such a build-up may otherwise come to a point where it risks becoming unstuck during an inhalation, giving the user too high a dose. The mouthpiece can easily be removed and replaced with a new one by the user. The suction tube is preferably part of the mouthpiece, so that the user exchanges the suction tube in the same operation as the exchange of the mouthpiece without any additional action. Preferably the user is notified by a noise or some other means emitted when the new mouthpiece is properly fitted.

As illustrated in FIG. 9 each dose carrier or cassette 4 carries one or more pre-metered doses of dry powder applied in the form of a strip 5 or a series of spots of powder. Each individual dose 31 has an airtight seal in the form of an aluminum foil 24 fixed on the top of a recess 7 in the cassette where the dose 31 is applied to a dose bed 6. The cassettes are individually packed in airtight bags to stop moisture and other substances from contaminating the cassettes. A cassette box 35 (FIG. 6) protects the cassette such that when the bag is opened and the cassette is removed the user does not come in direct contact with the cassette as illustrated in FIG. 5. The mechanically coded cassette (FIG. 6) 38 and cassette box are inserted into an opening 32, FIG. 3, in the inhaler body 8 intended for the purpose and correspondingly coded 38 such that only the correct type of cassette fits the opening. The coding eliminates the risk that a cassette carrying different powders than the intended is inserted in the inhaler.

FIG. 1 describes a complete cycle of operating the DPI by illustrating the actions performed by a user and the events, which the actions give rise to in a flow chart. Taking reference in the flow chart the operation of the present invention is illustrated.

Starting point in FIG. 1 is a step 100, i.e. the user starts with a completely new DPI and a sealed package containing the first cassette, which is to be loaded into the DPI. But first a dummy cassette loaded into the DPI upon delivery must be removed in a step 110. If the user is unfamiliar with the DPI, the dummy cassette can be used first to practice the art of inhalation, before loading a real cassette containing the powder doses. If the user decides to practice with the dummy it is necessary to do as many practice runs, as there are doses on the standard cassette before te dummy can be removed from the DPI.

Figure 6:
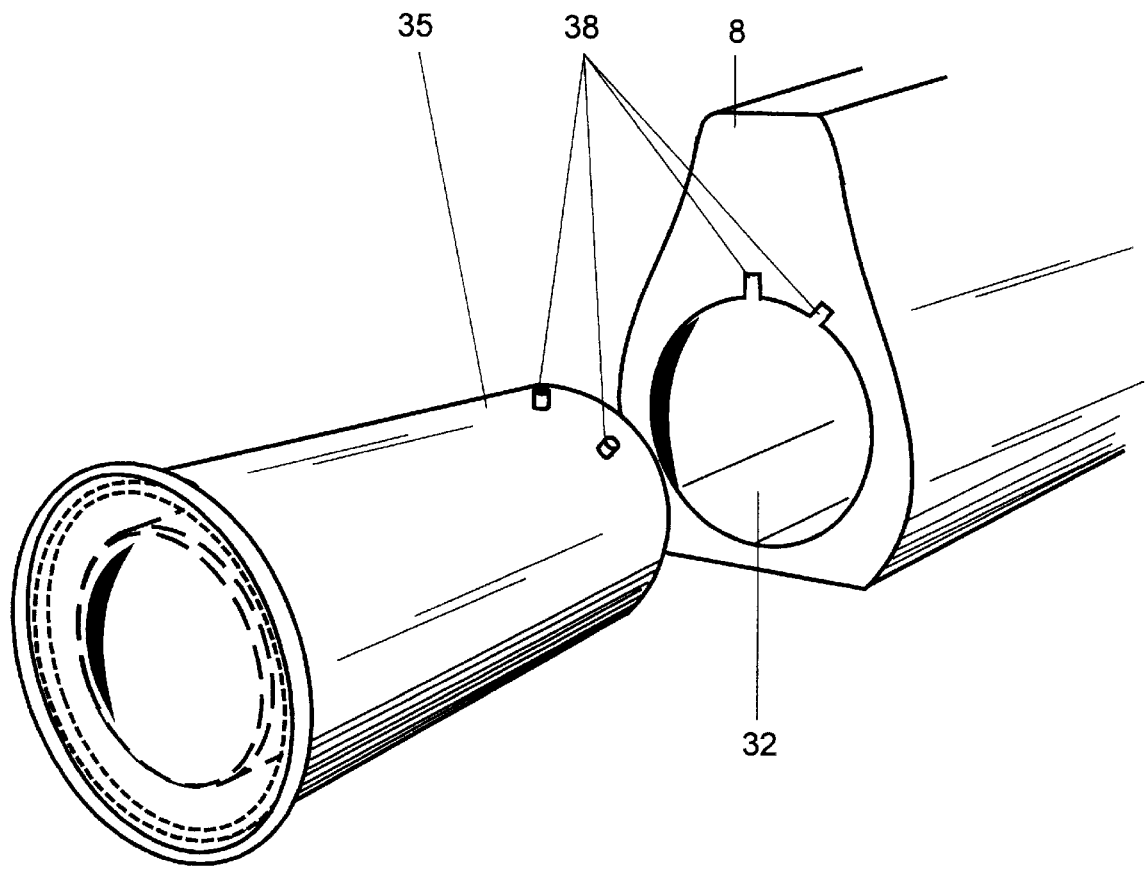
FIG. 6 shows in an illustrative embodiment the cassette in its protective box and illustrates a coding of the box/cassette and a corresponding coding of the cassette opening in the DPI body.

In next step 120, the user removes the cassette to be used with its protective box from the bag. The cassette with box, illustrated in FIG. 6, is then inserted in the opening 32 of the DPI in step 130, taking care that the coding of the cassette and box fit the corresponding coding of the opening. The coding is used to make it impossible to insert the wrong type of cassette into the DPI to make administration of the wrong drug impossible.

Figure 1:
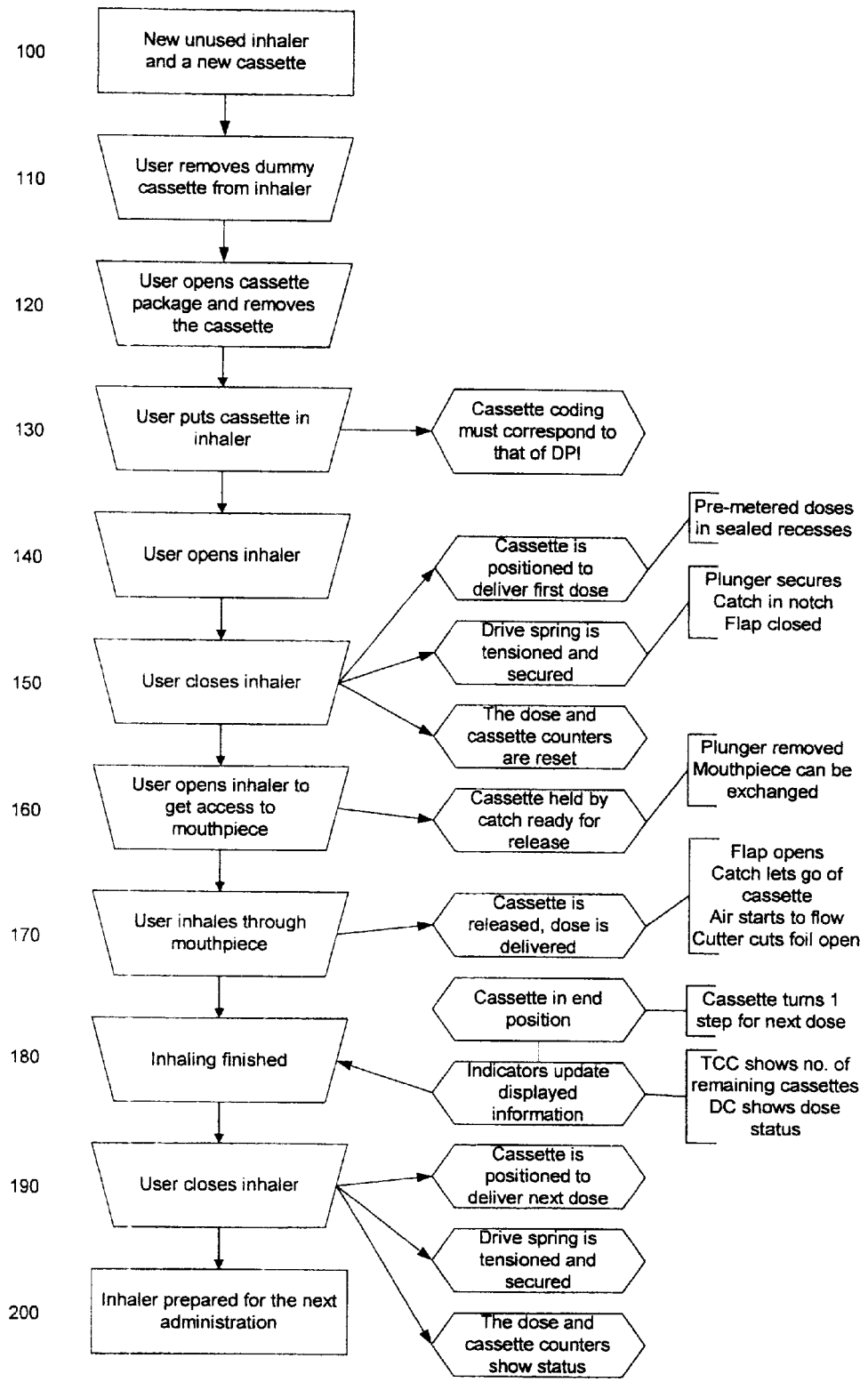
FIG. 1 illustrates a flow chart of a complete cycle of operating the dry powder inhaler according to the arrangement of the present invention.
Figure 2:
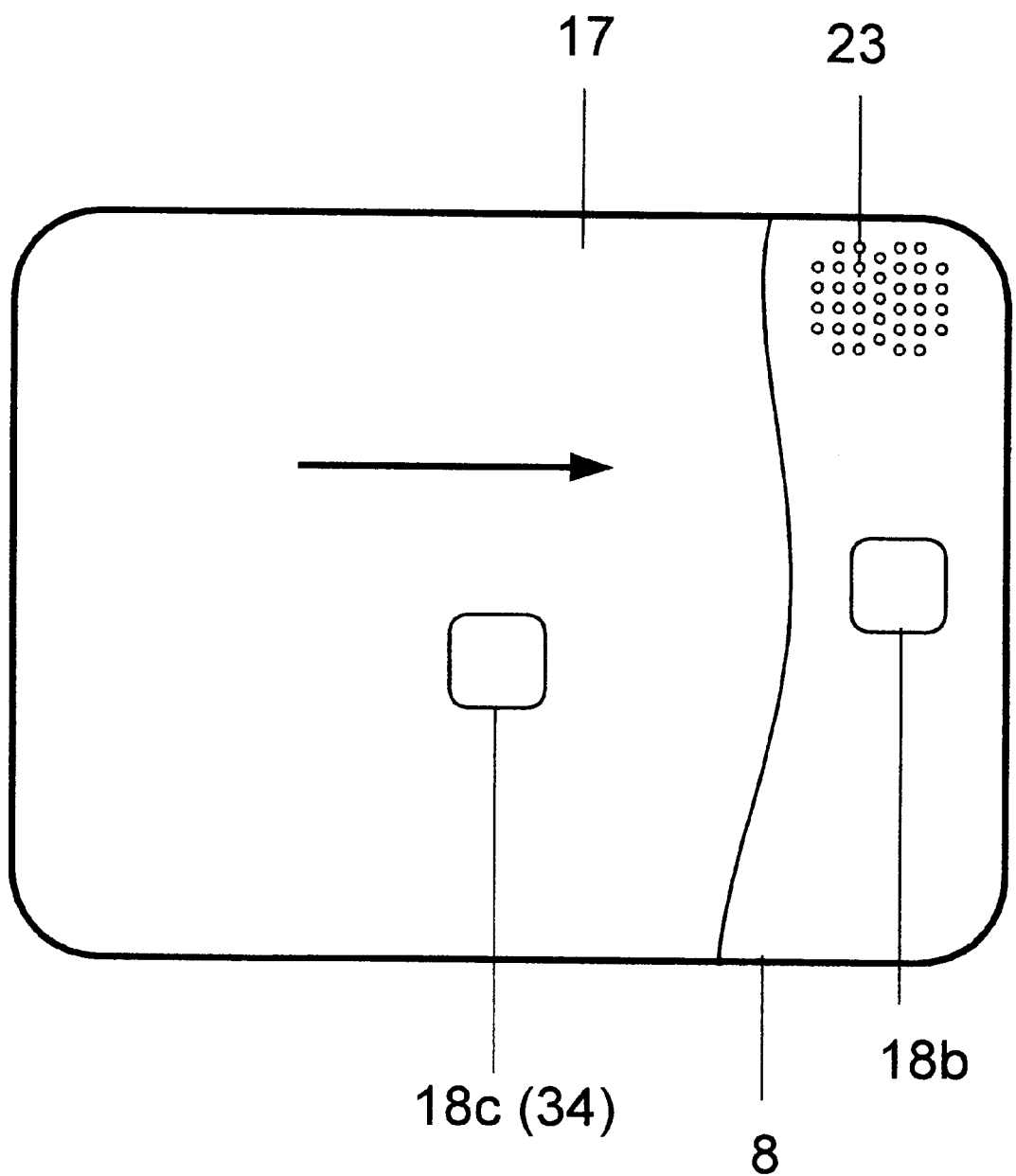
FIG. 2 illustrates in an illustrative embodiment a front view of the present inhaler in a closed state.
Figure 3:
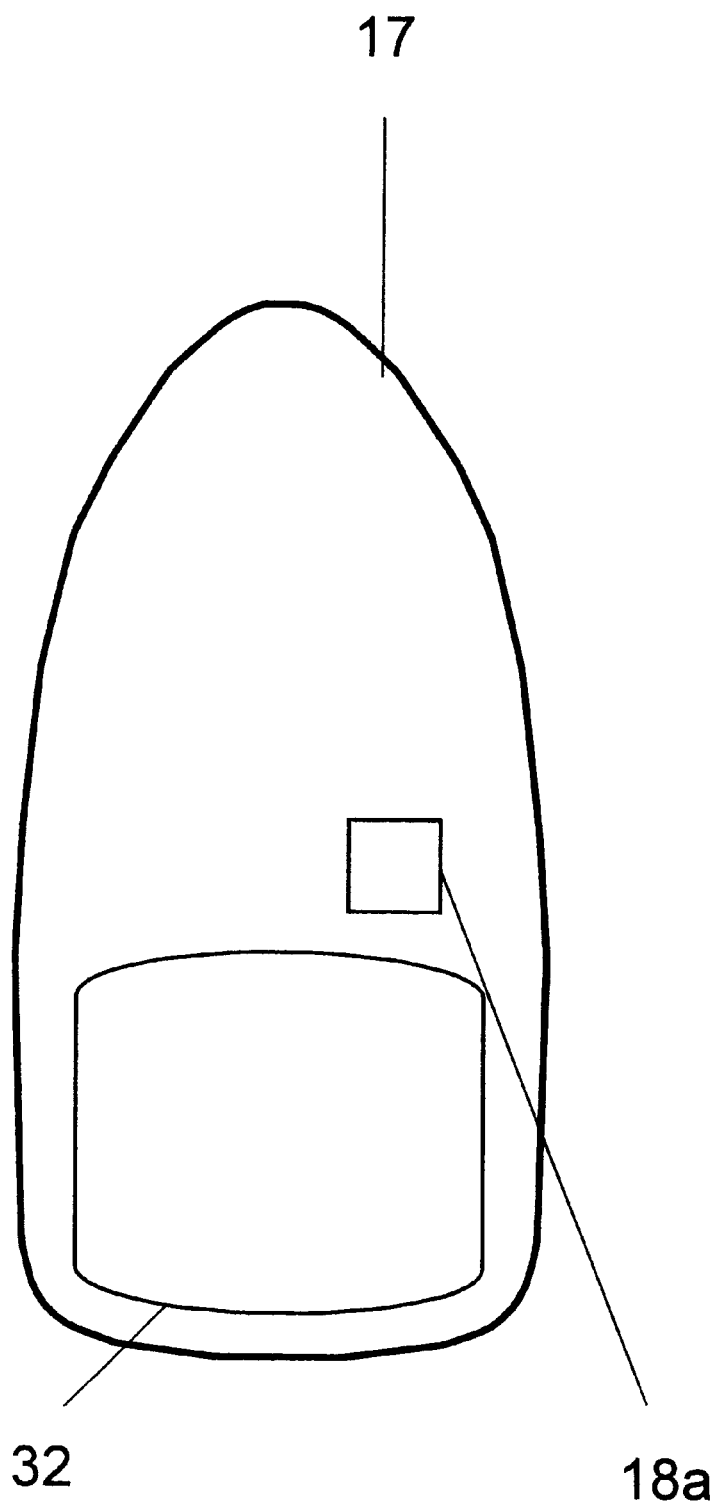
FIG. 3 illustrates in an illustrative embodiment the left side view of the inhaler in the closed state.
Figure 4:
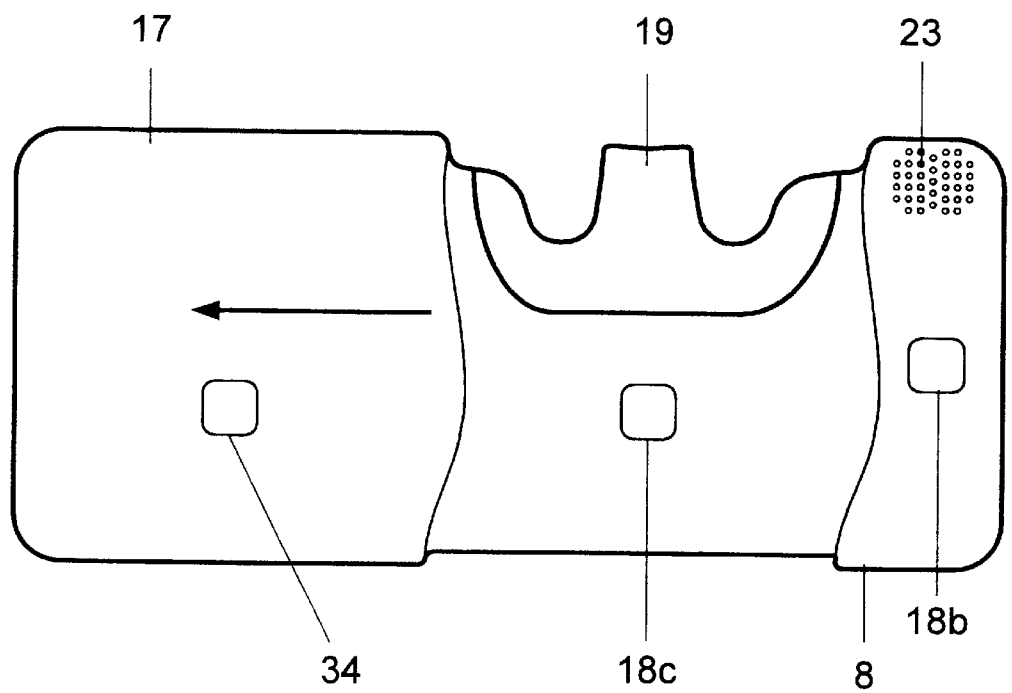
FIG. 4 illustrates in an illustrative embodiment a front view of the inhaler in the open operative state.

The DPI, schematically illustrated in FIGS. 2, 3 and 4, is opened as previously described, in step 140, and then closed again, in step 150. This action by the user accomplishes several things at the same time: i. The cassette is put in position to deliver the first dose. ii. The drive spring is tightened and secured in the tightened state by a plunger element, so that it cannot unleash accidentally and drive the cassette forward. iii. The dose and cassette counters are activated.

When the DPI is in the closed state no accidental administration can happen. The relevant internal moving parts of the DPI are statically and dynamically balanced using counterweights 15 and 29 as necessary, schematically illustrated in FIG. 10, making the DPI insensitive to external forces e.g. forces of inertia, gravitation, accidental blows etc. This means that the DPI is not sensitive to orientation for the inhalation, so the user can inhale in any position, with no negative effects on the administration process. Rough handling e.g. dropping the DPI to the floor when it is in the open state will not easily trigger the release of the cassette from its ready-to-go state.

In step 160 the user opens the inhaler to gain access to the mouthpiece in order to inhale a dose. In the process of opening the DPI the plunger element, securing the drive spring and the cassette, is removed but the cassette is still kept in position, ready to deliver a dose, by another catch mechanism.

The act of inhaling through the mouthpiece of the DPI in step 170 initiates the irreversible process of administering a dose to the user. A distinct sound is emitted from the DPI when the inhalation has triggered the administration of the dose, a preferably different series of sounds are emitted during the dose delivery and likewise a distinct sound is emitted when the delivery has come to an end, thereby notifying that the delivery has begun, when delivery is ongoing and when delivery has been successfully ended.

To start the dose administration process the body 8 of the DPI houses a system for triggering and controlling the administration of the doses from the cassette to the user. Illustrated in FIG. 10 the system for triggering the delivery to the user utilizes the inhalation effort to release the catch mechanism 12, which maintains the cassette in its initial spring loaded position as well as opens an inlet 23 for outside air to enter into the interior of the inhaler. The air passes a filter (not illustrated) at the inlet to stop dirt particles etc. from entering the DPI.

A moving flap 16 shuts the air inlet 23 tight when the user is not inhaling. The closing force emanates from a spring 13 acting through a system of levers 26 and 28 on the flap as well as on the catch mechanism that is keeping the cassette 4 from moving. When the user starts to inhale a differential pressure between the surrounding atmosphere and the airways of the user is induced. The induced differential pressure gives rise to an opening force, which counteracts the closing force onto the flap. When the differential pressure reaches and supersedes a well-defined minimum value the resulting opening force overcomes the force of the spring, releasing the catch 12, setting the cassette free and opening the flap so that air starts to flow into the inhaler. The minimum pressure differential required, or activation pressure, lies between 0.5 and 4 kPa, i.e. when the intended DPI is going from a ready state to a stage when the electro-dose is starting to be de-agglomerated inside the mouthpiece 19 and inhaled. This activation pressure is by no means strenuous for a user who is likely to feel that air starts to flow immediately after the inhalation has begun.

The system of levers connecting the spring with the catch and the flap is preferably designed using suitable low-friction materials. To minimize friction in the system according to the preferred embodiment it is preferably designed such that the surfaces of the parts 14, which are in contact with each other in order to transmit power from one to the other or vice versa, are made with rounded shapes and arranged such that the inevitable relative movement between the parts is not a rubbing action but a rolling action making the point of contact move like two cogs meshed in a gear wheel. In this way friction loss and consequently power loss in the mechanical system is minimized, which is important to achieve optimum overall performance of the DPI.

When the catch releases the cassette it is irreversibly propelled forward by the tensed drive spring 9. An airbrake 22 is exemplified by two embodiments schematically illustrated in FIGS. 11 and 12. The airbrake acts on the cassette to control the speed of motion of the cassette such that the time it takes for the cassette to pass by the fixed suction tube 33 of the mouthpiece is suitable with respect to the intended release time of powder for the inhalation process. The foil cutter 11 illustrated in FIGS. 9, 10 and 13 is used to cut and open up the aluminum foil (illustrated in FIG. 9) that seals a recess 7 carrying the pre-metered dose on the cassette surface. Thus, the foil 24 protects the dose 31 on the dose bed harboring in the recess. The cutter 11 sits in a fixed position such that when the cassette is pushed past the cutter it cuts through the protective foil and opens it up just in front of the nozzle 1, which is the inlet part of the suction tube 33. The cutter thus makes the dose accessible. As the cassette is pushed towards the nozzle the approaching layer or layers of powder particles of the dose get sucked up by the passing stream of air just before the inhaled air rushes into the nozzle. The particles are dispersed in the stream of air and continuously delivered to the user.

One of the problems inherent in inhaler devices is that the aerosolized substance tends to stick to the walls of the transport tube here referred to as the suction tube 33, which means that valuable substance of the dose may be retained within the suction tube in connection with each inhalation. The risk increases with every inhalation that the user gets an overdose if some of the accumulated retained substance suddenly becomes unstuck and is added to the dose that is being delivered during the inhalation. To eliminate this serious risk the new inhaler device uses an exchangeable mouthpiece 19 with a new design of the part acting as the suction tube 33, schematically illustrated in FIG. 8, comprising three portions; a nozzle 1, a diffuser 2 and a porous tube 3. The nozzle, which is very close to the powder source, is directly coupled to the diffuser, which in turn is connected to the porous tube. The stream of air sucked into the nozzle will carry the released powder into the diffuser.

The pressure drop of the DPI is the total pressure drop over the DPI and the major pressure drop within the DPI comes from the de-agglomeration of the electro dose in a relation $\Delta$Pde-agglomeration/$\Delta$Ptotal$\times$100>50%. This can be done by optimizing the aerodynamic construction of the mouthpiece and the device member and reducing the overall pressure drop inside the DPI. The mouthpiece should also be aerodynamically optimized to reduce retention of powder and electrically connected by a dissipative material to the user to eliminate electrical fields that will increase the retention in the mouthpiece.

The diffuser 2 is conical in shape and as the diameter of the diffuser increases with the distance from the nozzle the speed of the air decreases. In this way the total pressure loss can be kept to a low value. When the air reaches the porous tube 3 the airspeed is at or near optimum to make the delivery into the user's mouth as effective as possible for a local or system delivery to the deep lung of the precipitated powder particles of a narrow size distribution making up the pre-metered dose.

To obtain a deep lung delivery it is recommended that the inhalation airflow should be between 20 and 40 liters per minute not to have too high flows as the amount of impaction in the upper airways is a function of speed and having a dependency according to the amount of impaction as a function of inhalation airflow and the square of the particle size. An ideal design specification for a deep lung setting of the DPI is a flow 20 to 40 liters per 15 minute and a pressure drop between 1 and 2 kPa not to have too much constraint on the airways making them smaller and by this increasing the velocity of the air in the airways.

The local pressure inside the porous tube is lower than that on the outside, the surrounding atmosphere. The pressure differential will force the air to leak through the wall of the porous tube from the outside to the inside. By careful control of the parameters affecting the leakage, e.g. porosity of the wall, material density, wall thickness etc. an active non-sticking wall is created, which stops the aerosolized powder in the stream of air from sticking to the wall and getting retained within the suction tube. By careful selection of materials and combinations of materials and then applying the mentioned parameters it is possible to control exactly how much leakage and where the air leaks into the parts of the suction tube from the nozzle through the diffuser to the actual porous tube.

The airbrake comprises an enclosed but variable volume of air attached to the moving cassette and arranged such that the volume of air must contract or expand with the motion of the cassette. One or more vent holes of carefully controlled size let air in or out of the variable volume, thereby controlling the amount of leakage and consequently the effectiveness of the brake. To avoid malfunction of the airbrake through dirt or other matter sticking in the vent holes into the variable volume, the air coming into the DPI first passes through a fine mesh filter (not illustrated). The airbrake can be designed to have a variable leakage through the venting arrangement, thereby varying the braking force to suit the application. The airbrake 22 can also have an arrangement with a first part 21 of the airbrake 22 moving against a wall 20. The travel time of the cassette can therefore be set between e.g. 0.5 and 5 seconds and the speed characteristics can also be controlled in this manner.

The cassette is arranged so that there is a small time delay after the catch lets go of the cassette until the first part of the dose reaches the point where the powder in the dose is sucked up by the stream of inhaled air. In this short time span the inflow of air is built up and air begins to rush into the suction tube and the cassette accelerates up to speed such that the delivery of powder is at semi-stationary conditions right from the start.

In different embodiments of the present invention, the drive spring and the airbrake can be given different properties to achieve the desired speed characteristics in each embodiment depending on what is the primary purpose of the inhaler in each case. The dose is thus continuously administered for the length of time it takes for the dose, preferably in the form of a strip of powder, to pass by the nozzle. An ideal design specification for the dose delivery is for a deep lung delivery 1.5 seconds starting from the release of the cassette, and for a local lung delivery 0.75 seconds starting approximately 1 second after the release of the cassette, but possible to adjust within the total activation time for the DPI, i.e. from the opening to the closing of the air inlet, if necessary to ensure an optimized result. However, the total inhalation time should not be more than corresponding to 75% of the user's total inhalation volume. Investigations have shown that or users to have a comfortable inhalation through a DPI the pressure drop must normally be below 4 kPa and the flow rate between 20 and 80 liters/minute. When the inhalation stops, in step 180, the cassette is already at rest in its final position.

The user can check the number of remaining doses of the cassette presented at the dose counters 18b, 18c and 34, which window is active depends on whether the cassette is in the loaded or the unloaded state and if the cover is open or closed. If the inhaled dose was the last one of the cassette, the counter indicates this and it is not possible to perform any more inhalations without first exchanging the present cassette for a n e w one. If the present cassette is the last one of a set number, different for different DPIs with different types of cassettes, to be accepted by the DPI before scrapping, the cassette counter 18a indicates this. It is then not possible to remove the last cassette but the inhaler, including the mouthpiece together with the cassette is discarded.

In step 190 the user closes the DPI. If the cassette is used up at this point it must be exchanged for a new one. After a predetermined number of cassettes, the number depending on the type of cassette and the number of doses per cassette, the cassette counter indicates that the mouthpiece is used up and should be exchanged for a new one by the user, which is easy to do. The reasons for exchanging the mouthpiece are as mentioned previously two; to maintain a high standard of hygiene throughout the life of the inhaler and to eliminate the risk that retained powder in the suction tube comes unstuck during an inhalation, giving the user too high a dose.

The present dry powder inhaler, DPI provides a general device for dispensing powder for inhalation, particularly electro-powder in the form of pre-metered electro-doses. As the present DPI is apt to individually be adapted to every specific kind of electro-powder it will then also constitute an inhaler meeting the requirements for an electrostatic dry powder inhaler, also referred to as an EDPI. It will be obvious to a person skilled in the art that the inhaler device may be modified and changed in many ways without departing from the scope of the present invention, which is defined by the appended claims.

What is claimed is:

1. An inhaler device in combination with an exchangeable dosing member for respiratory administration of an inhalation powder into the deep or upper lung airways, comprising:

a compact integrated assembly including a movable case having first and second states, the first state with a sliding cover in a closed position enclosing an exchangeable mouthpiece, and the second state with the sliding cover in an open position exposing said exchangeable mouthpiece, the assembly in the second state being loaded and ready to deliver a prepared dose of medical powder upon an inhalation;

a powder dose of the exchangeable dosing member being a dry powder substance or dry powder medical formulation prepared for a prolonged dosing sequence by said inhaler device controlling an activation time between 0.5 and 5 seconds for controlling a dose delivery time set within an activation time of said inhaler device, said exchangeable dosing member further providing a plurality of sequentially accessible doses;

said exchangeable dosing member being a sealed dosing cassette and preserving a controlled water content and electrostatic state during a total life time of the sealed dosing cassette, a seal of the sealed dosing cassette being a foil, the foil sealing a dose being cut open when the device has been moved into the second state by moving the sliding cover to the open position, and when a user initiates an inhalation by sucking air through the exchangeable mouthpiece.

2. The inhaler device according to claim 1, comprising dissipative or conductive materials in at least one of the mouthpiece and the exchangeable dosing member to prevent electrostatic charge build-up during inhalation.

3. The inhaler device according to claim 1, wherein said exchangeable mouthpiece is integrated with a suction tube comprising a nozzle, a diffuser and a porous tube for adjusting speed of air to an optimum to make delivery of powder into a user's mouth effective for a delivery of the precipitated dose of powder particles to the deep lung.

4. The inhaler device according to claim 3, wherein said nozzle is adjacent to and movable over a pre-metered dosed powder on the sealed dosing cassette immediately after the sealing foil has been opened for access.

5. The inhaler device according to claim 1, wherein said exchangeable dosing member is mechanically coded to only fit into an inhaler intended for a particular medical powder composition to prevent utilization of an incorrect drug.

6. The inhaler device according to claim 1, wherein the inhaler device further comprises dose and cassette indicators on the assembly being activated when a first exchangeable dosing member in a form of the sealed dosing cassette containing pre-metered doses of inhalation powder is inserted into the assembly.

7. The inhaler device according to claim 6, wherein said dose indicator, after a release of a last dose from a present dosing cassette, denotes an exchange of the sealed dosing cassette before a next inhalation of a dose can be initiated, whereby an inserted cassette in use can not be exchanged before a last pre-metered dose has been released.

8. The inhaler device according to claim 6, wherein said dose indicator, after a preset number of doses inhaled, denotes an exchange of the mouthpiece.

9. The inhaler device according to claim 6, wherein said cassette indicator keeps track of a number of already exchanged cassettes and when a preset number of cassettes has been reached a last cassette will be locked in the inhaler after a last dose has been emitted, marking that the inhaler device now should be discarded for a new one.

10. The inhaler device according to claim 1, wherein a new inhaler is supplied with an empty dosing cassette for user exercises that is exchangeable for a dosing cassette containing pre-metered prepared doses of powder.

11. The inhaler device according to claim 10, wherein when said empty dosing cassette if not directly exchanged for a dosing cassette with pre-metered doses, but is utilized for exercises, has to perform a plurality of simulated inhalation operations corresponding to a number of doses contained by a particular type of dosing member, to be able to perform an exchange for a dosing cassette containing doses as controlled by the assembly.

12. The inhaler device according to claim 1, wherein said exchangeable dosing member contains electrostatically deposited dry medical powder.

13. The inhaler device according to claim 1, wherein the inhaler device is a dry powder inhaler (DPI) and a sound is emitted from the dry powder inhaler when an inhalation has triggered administration of the powder dose, a different series of sounds being emitted during a delivery of the powder dose and a distinct sound being emitted from the DPI when the delivery has come to an end, thereby notifying the user that a delivery has begun, when a delivery is ongoing and when a delivery has been successfully ended.

14. The inhaler device according to claim 1, wherein a braking arrangement controls a prolonged dosing sequence of the inhaler device.

15. The inhaler device according to claim 1, wherein said exchangeable mouthpiece optimizes the inhaler device to an optimum pressure between 0.5 and 4 kilopascals and an airflow between 20 and 80 liters per minute with respect to the medical powder being inhaled.

16. The inhaler device according to claim 1, wherein a foil cutter adjacent to the mouthpiece, cuts open a foil sealing a dose loaded onto a movable dose member, when said case is in said second state and immediately before a dose is accessed and sucked up into the mouthpiece, so that a time of dose exposure to ambient air is made so short to be insignificant, resulting in no deterioration of dose quality before the dose is inhaled.

17. A combination of a dry powder inhaler device and an exchangeable dosing member comprising:

an inhaler body;

a cover of said inhaler body being movable from a first position to cover an exchangeable mouthpiece, to a second position to expose said exchangeable mouthpiece;

a means for controlling an activation time to release a powdered dose of the exchangeable dosing member over a prolonged period, said exchangeable dosing member having a plurality of powdered doses; and a sealing member covering said plurality of powdered doses, said sealing member being opened when said cover has been moved to said second position, and when a user initiates an inhalation by sucking air through the exchangeable mouthpiece.

* * * * *